| United States Patent [19] | [11] Patent Number: 4,473,494 |
| Tye | [45] Date of Patent: Sep. 25, 1984 |

[54] PREPARATION OF STROMA-FREE, NON-HEME PROTEIN-FREE HEMOGLOBIN

[75] Inventor: Ross W. Tye, Sausalito, Calif.

[73] Assignee: The United States of America as represented by the Secretary of the Army, Washington, D.C.

[21] Appl. No.: 497,455

[22] Filed: May 4, 1983

[51] Int. Cl.³ .................... A61K 35/14; A61K 37/04; C07C 103/52
[52] U.S. Cl. ...................... 260/112 B; 260/112.5 R; 424/101; 424/177
[58] Field of Search .................... 260/112 B, 112.5 R

[56] References Cited

U.S. PATENT DOCUMENTS

| 3,991,181 | 11/1976 | Doczi | 424/101 |
| 4,001,401 | 1/1977 | Bonsen et al. | 260/112 B |
| 4,376,059 | 3/1983 | Davis et al. | 260/112 B X |

OTHER PUBLICATIONS

J. of Exptl. Med., 126, 1127–1142, (1967), Rabiner et al.
Hemoglobin 6(2), 183–186, (1982), Lehmann et al.

Primary Examiner—Howard E. Schain
Attorney, Agent, or Firm—John H. Raubitschek; John M. Petruncio; Werten F. W. Bellamy

[57] ABSTRACT

A method for the production of stroma-free, non-heme protein-free hemoglobin by use of zinc ion to promote precipitation of a zinc ion-bound insoluble hemoglobin complex, followed by membrane ultrafiltration of the zinc-hemoglobin complex from the filtrate fluid medium, preferably with a saline dialyzate.

10 Claims, No Drawings

PREPARATION OF STROMA-FREE, NON-HEME PROTEIN-FREE HEMOGLOBIN

BACKGROUND OF THE INVENTION

The need for a purified preparation of hemoglobin as a starting material for use as a resuscitation fluid was first recognized by Rabiner, *Journal of Exp. Med.,* 126, 1127 (1967). He was able to remove a large amount of the stromal elements and demonstrate that most of the toxic properties of hemolyzed red cells were related to the membranes (stroma) and associated lipids. Subsequent to his demonstration that hemoglobin was compatible as an additive into the intravascular system, many workers modified his initial production scheme. Doczi, U.S. Pat. No. 3,991,181, discloses a method which makes extensive use of centrifugation to wash the red blood cells with various saline solutions prior to hemolysis in hypotonic phosphate buffers. He then removes the stromal contamination by ultrafiltration on an $0.22\mu$ filter, dialyzes the filtrate to achieve crystalloid composition compatible with physiological systems, and filters the solution through a stack of filters $8\mu$ to $0.22\mu$ to remove protein aggregates and bacteria thus sterilizing the filtrate prior to use or storage. It is in fact pertinent to realize that the process simply has removed the membrane from the red cell and has kept the entire contents of the red cell including a 5% by weight non-heme protein.

Bonson et al., U.S. Pat. No. 4,001,401, described a method using washed rbc's, hypotonic lysis, centifugation and repeated centifugation after toluene extraction. They also use dialysis to gain crystalloid physiological compatibility. Again the final solution contains the entire content of the erythrocyte. DeVenuto et al. continued the prior art of Bonson et al. by adding the additional step of crystallization from concentrated Hb solution (14%) in 2.8 M potassium phosphate pH 6.8 buffer. This was the first method that attempted to remove non-heme protein from the stroma-free hemoglobin solution. Using many techniques it is easy to show that crystallization does not remove non-heme protein efficiently and repeat recrystallization does not increase the purity.

Another significant problem exists in the task of collecting outdated red blood cells from hospitals and blood banks throughout the United States and the world, for use in the production of a hemoglobin based blood substitute. If the outdated blood must be washed at the collection center and/or stored and refrigerated prior to shipping on a bimonthly basis, compliance for collection will be decreased. Alternately, if the outdated blood could be frozen and shipped when sufficient units were collected to warrant collection, the compliance would be greater. None of the methods mentioned above for isolating hemoglobin have been used to isolate hemoglobin from hemolyzed blood containing serum proteins and unwashed red blood cells.

Recently Carrell and Lehmann, *J. Clin. Path.,* 34, 796 (1981) and Lehmann et al., Li Hemoglobin, 6(2), 183–186 (1982) reported the use of zinc ion to precipitate unstable and normal hemoglobins from dilute solutions between analytical methodologies. The precipitated hemoglobin was incubated at 37° C. for 15 min., collected by centrifugatio and resolubilized by EDTA.

A need exists for a method to purify hemoglobin in large quantities, free of stroma, serum proteins and non-heme intraerythrocytic proteins. Minimal standards for such hemoglobin were set by a committee of U.S. Army researchers preparing stroma-free hemoglobin for modification and use as a blood substitute. Only hemoglobin made by the process of this invention meet these standards which follows:

(a) non-heme protein—$<0.1\%$
(b) stromal elements—undetectable
(c) lipids—$<0.001\%$
(d) endotoxin—pass LAL Thus hemoglobin can be prepared from either frozen whole blood or preferably washed cells hemolyzed in hypotonic buffer used to make the initial stroma-free Hb.

SUMMARY OF THE INVENTION

This invention is directed to a method for the production of stroma-free, non-heme protein-free hemoglobin by use of zinc ion to promote precipitation of a zinc ion-bound insoluble hemoglobin complex, followed by membrane separation of the zinc-hemoglobin complex from the non-heme protein-containing filtrate fluid medium. The zinc-hemoglobin complex is preferably further purified by a dialysis step using ultrafiltration or membrane separation with a saline dialyzate. More particularly, practice of this invention allows for removal of non-heme proteins from stroma-free hemoglobin by a method comprising promoting precipitation of a zinc ion-bound insoluble hemoglobin complex by allowing a solution of stroma-free hemoglobin to complex with an at least tenfold molar excess of soluble zinc salt.

The zinc ion-bound hemoglobin complex precipitate is then separated from the filtrate fluid containing the non-heme protein by use of a membrane having a pore size in the range of about $0.22\mu$ to about $0.5\mu$.

The stroma-free hemoglobin from which the non-heme protein is to be removed is generally produced by crystallization, centrifugation or preferably ultrafiltration.

The stroma-free hemoglobin can be derived from a human, or can be, for example, bovine, ovine or porcine.

The concentration of the solution of stroma-free hemoglobin is generally about 7 g%. Preferably, this solution is diluted to less than 0.5 g% prior to treatment with the zinc salt.

The solution of stroma-free hemoglobin is also preferably adjusted to a salinity in the range of 50 to 250 mM and a pH in the range of 7 to 9, more preferably about 7.5.

An additional preferable embodiment of this invention includes treating the separated zinc-ion bound hemoglobin complex precipitate with a solubilizing solution quantity of a zinc-chelating compound such as ethylenediaminetetraacetic acid (EDTA) and refiltering the released hemoglobin through the membrane initially used to separate the precipitated complex.

The uses of this procedure for the precipitation of hemoglobin as a complex with zinc ion include:

(1) Purification of hemoglobin from the non-heme proteins within the erythrocyte
(2) concentration of hemoglobin from dilute solutions
(3) purification and concentration of hemoglobins from other sources such as bovine
(4) purification and concentration of hemoglobins after modification
(5) purification and concentration of hemoglobin from plasma proteins (6) recycling of hemoglobin through the procedure to obtain ultrapure material for clinical or analytical standards.

Use of the method of this invention allows for the rapid removal of non-heme proteins from the erythrocyte contents to allow for the preparation of 99.9% pure hemoglobin in large volume quantities suitable for pharmaceutical preparation of hemoglobin as a blood substitute. For instance one operator with one unit of equipment can process one hundred units (500 mls) of outdated human red blood cells to yield roughly six kilograms of non-heme protein-free highly purified hemoglobin in an eight hour shift.

DETAILED DESCRIPTION OF THE INVENTION

The following flow diagram is provided to illustrate the method of this invention for the Isolation and Purfication of Hb from erythocytes.

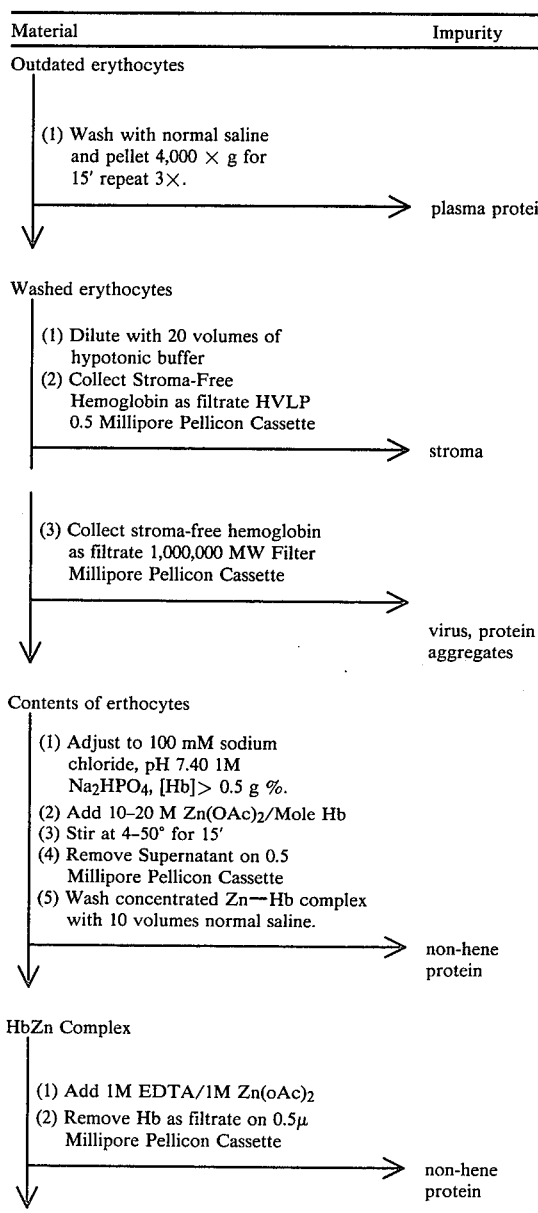

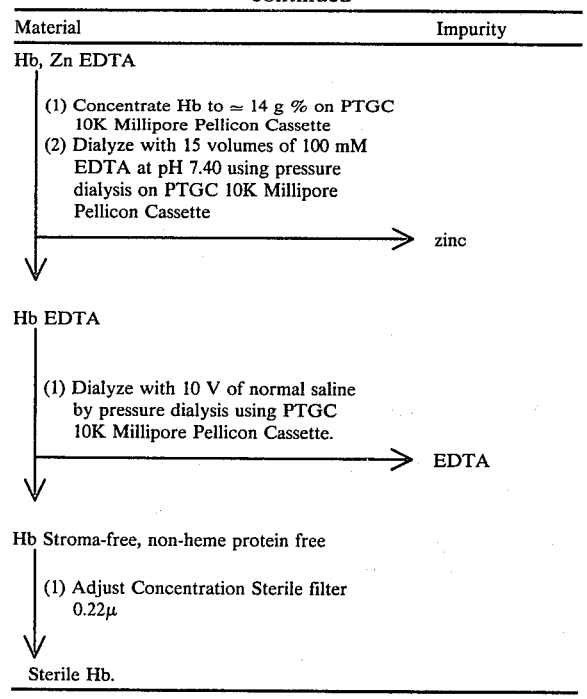

The preparation of hemoglobin free of greater than 98% of the non-heme protein found in the erythrocyte can be accomplished by precipitation of the hemoglobin as a zinc complex by the addition of zinc acetate to a dilute hemoglobin solution with a pH between 7.2 abd 7.6.

The precipitation of hemoglobin by zinc ion at a 10:1 Molar ratio includes a specific high affinity ligand relationship for these two ions. This uniqueness is unlike ammonium sulfate or ethanol protein precipitation which organizes the water molecules in solution and excludes the protein, resulting in precipitaton. The zinc hemoglobin complex is able to satisfy all the charge interactions without solvent interaction and precipitates without changing the environment for all of the protein molecules in general. It is thus unique and specific for hemoglobin.

Hemoglobin may be released from the erythrocyte by hypotonic lysis in twenty volumes of deionized water. Other methods of erythrocyte lysis such as "slow hypotonic lysis" or "freeze thaw", may also work well. The stroma is removed by ultrafiltration of the hemolysate on a $0.5\mu$ filter which retains the cellular components and passes the hemoglobin. This step is performed at 4° C. as rapidly as possible after hemolysis of the erythrocyte. Other methods of removing stroma may also be used.

The dilute solution of filtered hemoglobin or similar solution has the following general characteristics. It has a final pH>7.0, usually between 7.2 and 7.6 adjusted with 1M $Na_2HPO_4$. It has a Hb concentration of <0.5 gram % w/v and it may be any temperature 4°–50° C. Other buffers will work, but the salts and buffers used must not form precipitates with zinc ion. The precipitation works best saline solutions with ionic strength between 0.050 and 0.250M.

At least ten moles of Zn ion are added per mole of hemoglobin. The addition is dropwise with stirring to allow a complete precipitation. The suspension is allowed to stir for fifteen minutes at temperature from 4°–37° C. Higher temperatures make the precipitate easier to collect but are not necessary and increase the amount of denatured hemoglobin.

The precipitate is collected by filtration on a Millipore Pellicon cassette HVLP 0.5μ the non-heme protein is removed in the filtrate. When the zinc hemoglobin is concentrated to a reasonably small volume it is washed using 10 volumes of normal saline to further remove the non-heme protein. The hemoglobin is resuspended by the addition of one mole of EDTA per mole of zinc added and sufficient volume of saline solution to achieve a 14% solution or less as desired. This solution is collected as a filtrate from the 0.5μ cassette.

Removal of Zinc, EDTA and Tris buffers is accomplished by dialysis. A convenient method is to use fifteen volumes of dialysis fluid on a pressure dialysis system such as the Millipore Pellicon 10,000 Mwt Cassette, using 100 mM EDTA ph 7.40 followed by 15 volumes of normal saline.

After dialysis the pH of the material is adjusted to 7.40 with 0.1M HCL or NaOH and sterile filtered using an 0.22 filter into a sterile container.

Additional variations of the subject method will be apparent to the skilled artisan. These modifications are to be considered within the scope of the claims to this invention which follow.

I claim:

1. A method for the production of stroma-free, non-heme protein-free hemoglobin comprising
   promoting precipitation of a zinc ion-bound insoluble hemoglobin complex by allowing a solution of stroma-free hemoglobin to complex with an at least tenfold molar excess of soluble zinc salt, then
   ultrafiltering said zinc ion-bound hemoglobin complex precipitate from the filtrate fluid containing the non-heme protein by use of a membrane having a pore size in the range of about 0.22μ to about 0.5μ.

2. The method according to claim 1 wherein the stroma-free hemoglobin is produced by crystallization, centrifugation, or ultrafiltration.

3. The method according to claim 1 wherein the stroma-free hemoglobin is derived from a human, or is bovine, ovine or porcine.

4. The method according to claim 1 wherein the solution of stroma-free hemoglobin is diluted to less than 0.5 g% prior to precipitation by zinc ion and said zinc ion-bound hemoglobin complex precipitate is dialyzed with normal saline by said ultrafiltration.

5. The method according to claim 1 wherein the solution of stroma-free hemoglobin is adjusted to a salinity in the range of 50 to 250 mM.

6. The method according to claim 1 wherein the stroma-free hemoglobin has a pH in its range of 7 to 9.

7. The method according to claim 6 wherein the pH is about 7.5.

8. The method for the production of stroma-free, non-heme protein-free hemoglobin according to claim 1 further comprising
   treating the ultrafiltered zinc-ion bound hemoglobin complex precipitate with a solubilizing solution quantity of EDTA, and refiltering the released hemoglobin through said membrane.

9. A method for the production of stroma-free, non-heme protein-free hemoglobin comprising
   promoting precipitation of a zinc ion-bound insoluble hemoglobin complex by allowing less than 0.52% solution of ultrafiltered stroma-free hemoglobin derived from a human to complex with an at least tenfold molar excess of soluble zinc salt, said stroma-free hemoglobin solution having a salinity in the range of 50 to 250 mM and a pH in the range of 7 to 9,
   ultrafiltering with a saline dialyzate said zinc-ion bound hemoglobin complex precipitate from the filtrate fluid containing the non-heme protein by use of a membrane having a pore size in the range of about 0.22μ to about 0.5μ,
   treating the ultrafiltered zinc-ion bound hemoglobin complex precipitate with a solubilizing solution quantity of ethylenediaminetetraacetic acid, and
   refiltering the released hemoglobin through said membrane.

10. A method according to claim 9 wherein the pH of the strome-free hemoglobin solution is about 7.5.

* * * * *